US009173933B2

(12) United States Patent
Weigl et al.

(10) Patent No.: US 9,173,933 B2
(45) Date of Patent: Nov. 3, 2015

(54) RECOMBINANT MODIFIED VACCINIA VIRUS ANKARA INFLUENZA VACCINE

(75) Inventors: Josef Weigl, München (DE); Jürgen Hausmann, Gundelfingen (DE); Robin Steigerwald, München (DE)

(73) Assignee: BAVARIAN NORDIC A/S, Kvistgaard (DK)

( * ) Notice: Subject to any disclaimer, the term of this patent is extended or adjusted under 35 U.S.C. 154(b) by 71 days.

(21) Appl. No.: 13/877,218

(22) PCT Filed: Oct. 7, 2011

(86) PCT No.: PCT/EP2011/004996
§ 371 (c)(1),
(2), (4) Date: Apr. 1, 2013

(87) PCT Pub. No.: WO2012/048817
PCT Pub. Date: Apr. 19, 2012

(65) Prior Publication Data
US 2013/0183335 A1    Jul. 18, 2013

Related U.S. Application Data

(60) Provisional application No. 61/393,838, filed on Oct. 15, 2010.

(30) Foreign Application Priority Data

Mar. 2, 2011  (EP) ..................................... 11001749

(51) Int. Cl.
| | | |
|---|---|---|
| A61K 39/275 | (2006.01) | |
| A61K 39/145 | (2006.01) | |
| C12N 15/86 | (2006.01) | |
| A61K 39/12 | (2006.01) | |
| A61K 39/00 | (2006.01) | |

(52) U.S. Cl.
CPC ............... *A61K 39/145* (2013.01); *A61K 39/12* (2013.01); *C12N 15/86* (2013.01); *A61K 2039/5254* (2013.01); *A61K 2039/5256* (2013.01); *A61K 2039/545* (2013.01); *A61K 2039/55* (2013.01); *C12N 2710/24143* (2013.01); *C12N 2760/16134* (2013.01); *C12N 2760/16234* (2013.01)

(58) Field of Classification Search
None
See application file for complete search history.

(56) References Cited

U.S. PATENT DOCUMENTS

2008/0003239 A1*  1/2008  Duke et al. ................. 424/206.1

FOREIGN PATENT DOCUMENTS

| EP | 1 925 318 A1 | 5/2008 |
|---|---|---|
| WO | 02/42480 A2 | 5/2002 |
| WO | 03/097845 A1 | 11/2003 |
| WO | 2010/134094 A1 | 11/2010 |
| WO | 2011/087839 A1 | 7/2011 |

OTHER PUBLICATIONS

Poon et al: "Vaccinia Virus-Based Multivalent H5N1 Avian influenza Vaccines Adjuvanted with IL-15 Confer Sterile Cross-Clade Protection in Mice", Journal of Immunology, vol. 182, No. 5, Mar. 1, 2009, pp. 3063-3071.
Rimmelzwaan et al: "Candidate influenza vaccines based on recombinant modified vaccinia virus Ankara", Expert Review of Vaccines, vol. 8, No. 4, 2009, pp. 447-454.
Kilbourne: Nature Medicine, vol. 5, No. 10, Oct. 1, 1999, pp. 1119-1120.
Du et al: "Research and development of universal influenza vaccines", Microbes and Infection, vol. 12, No. 4, Apr. 1, 2010, pp. 280-286.
Adar Y et al: "A universal epitope-based influenza vaccine and its efficacy against H5N1", Vaccine, vol. 27, No. 15, Mar. 26, 2009, pp. 2099-2107.
Goodman et al: HA Human Multi-Epitope Recombinant Vaccinia Virus as a Universal T Cell Vaccine Candidate against Influenza Virus, PLOS ONE, vol. 6, No. 10, Jan. 1, 2011, pp. E25938-E25938.
Berthoud et al: "Potent CD8+ T-cell immunogenicity in humans of a novel heterosubtypic influenza A vaccine, MVA-NP+M1.", Clinical Infectious Diseases : An Official Publication of the Infectious Diseases Society of America, vol. 52, No. 1, Jan. 1, 2011, pp. 1-7.
Kreijtz et al: "Preclinical evaluation of a modified vaccinia virus Ankara (MVA)-based vaccine against influenza A/H5N1 viruses", Vaccine, Elsevier Ltd, GB, vol. 27, No. 45, Oct. 23, 2009, pp. 6296-6299.
Hessel et al: "A Pandemic Influenza H1N1 Live Vaccine Based on Modified Vaccinia Ankara is Highly Immunogenic and Protects Mice in Active and Passive Immunizations", PLOS ONE, vol. 5, No. 8, Jan. 1, 2010, pp. E12217-E12217.

* cited by examiner

*Primary Examiner* — Stacy B Chen
(74) *Attorney, Agent, or Firm* — Law Office of Salvatore Arrigo and Scott Lee, LLP

(57) ABSTRACT

The invention concerns a recombinant modified vaccinia virus Ankara (MVA virus) expressing at least two external influenza virus antigens and/or an epitope of one or more of the at least two antigens and at least two internal influenza virus antigens and/or an epitope of the at least two antigens. The invention, thus, concerns a recombinant MVA virus encoding multiple external and/or internal influenza virus antigens, preferably from multiple influenza virus strains. The invention further concerns the use of said recombinant MVA in preparing a medicament and vaccine for influenza virus. Further encompassed by the present invention are methods, composition and kits.

20 Claims, 8 Drawing Sheets

**MVA-*PanFlu***
Polyvalent vaccine: HA genes of 4 high risk strains

| | | | | |
|---|---|---|---|---|
| ④ | ① | ② | ③ | consecutive insertion #: |
| MVA-mBN210 | MVA-mBN208 | MVA-mBN209 | MVA-mBN207 | resulting virus |
| pBN395 | pBN367 | pBN368 | pBN366 | recombination plasmid |
| IGR 44/45 | IGR 64/65 | IGR 88/89 | IGR 148/149 | intergenic region |

H7 — H2 NA — H9 M2 — H5 M1 PB-1 NP
fusion gene

RECOMBINANT MODIFIED VACCINIA VIRUS ANKARA INFLUENZA VACCINE

This application is the U.S. National Stage of International Application PCT/EP2011/004996, filed Oct. 7, 2011, which claims the benefit of European Application 11001749.8, filed Mar. 2, 2011, and U.S. Provisional Appln. 61/393,838, filed Oct. 15, 2010. All of these applications are incorporated herein by reference.

The invention concerns a recombinant modified vaccinia virus Ankara (MVA virus) expressing at least two external influenza virus antigens and/or an epitope of one or more of the at least two antigens and at least two internal influenza virus antigens and/or an epitope of the at least two antigens. The invention, thus, concerns a recombinant MVA virus encoding multiple external and/or internal influenza virus antigens, preferably from multiple influenza virus strains.

The invention further concerns the use of said recombinant MVA in preparing a medicament and vaccine for influenza virus. Further encompassed by the present invention are methods, composition and kits.

BACKGROUND

Yearly, influenza virus causes approximately 500,000 deaths (Brown et al. 2009, Immunology and Cell Biology 87, 300-308). With the emergence of a novel viral subtype, deaths can rise into the millions. Id. For example, the pandemic of 1918-1919 killed more than 40 million people, and this was when rapid air travel was much less common (Doherty et al. 2008, The Journal of Clinical Investigation 118, 3273-3275).

Given the fact that the hemagglutinin surface proteins (HA) exist in 16 subtypes, the neuraminidase (NA) in nine subtypes, and the potential for recombination exists in the animal kingdom as well as in the human, many potential pandemic influenza A virus candidates exist. Once an influenza virus has become a seasonal virus, usually after a pandemic, it is going to drift or change over time. Several seasonal viruses are presently in co-circulation: An influenza A virus of the subtype H3N2, and another of the subtype H1N1, and two influenza virus type B strains from the Yamagata and the Victoria lineages. After the recent swine flu pandemic, the new variant of the influenza A H1N1 subtype (vH1N1 or H1N1 new) became the new seasonal H1N1 strain.

In any case, approaches for pandemic influenza vaccines, as well as seasonal influenza vaccines, warrant a combination of several influenza viruses. For pre-pandemic vaccines, a combination of several strains into one vaccine candidate is indicated to either prime against several viruses simultaneously in a pre-pandemic setting or to limit a stockpile to a few vaccines (vaccine library), but each vaccine with a multivalent option, i.e. being protective against several strains to increase its potential.

At present, seasonal vaccines should cover at least three strains, two A-strains and one B-strain.

In this way, the concept of multivalency is motivated by different reasons with regard to pandemic versus seasonal vaccines, but practically leading to similar vaccine construct approaches.

For priming in naïve populations, for a pandemic vaccine generally the entire population and for a seasonal vaccine the young children, an induction of immunity as similar as possible to the wild virus infection in regard to internal and external antigens is desired. For boosting vaccination in subjects already primed by either a wild type influenza (sometimes also called "flu" herein) infection or a flu vaccination, pre-existing immunity should not prohibit a sufficient booster response. Priming can consist of one or several doses (a priming schedule) and boosting most often of only one vaccination.

The principal mechanism of action of current subunit or inactivated, detergent-disrupted influenza virus vaccines is to induce neutralizing antibodies (Doherty et al. 2008, The Journal of Clinical Investigation 118, 3273-3275). Commonly used inactivated seasonal influenza vaccines induce protective antibody responses against the immunizing virus strains (Brown et al. 2009, Immunology and Cell Biology 87, 300-308). However, the antibody response may not be effective against novel virus strains. Id. Antigenic drift occurs in both type A and type B influenza and results in neutralization-resistant mutants. Id. Thus, it is necessary to constantly produce new vaccines to combat these new strains.

MVA (modified vaccinia virus Ankara) originates from the dermal vaccinia virus strain chorioallantois vaccinia virus Ankara (CVA) that was maintained in the Vaccination Institute, Ankara, Turkey for many years and used for vaccination of humans. Due to the often severe post-vaccinal complications associated with vaccinia viruses, there were several attempts to generate a more attenuated, safer smallpox vaccine.

During the period of 1959 to 1974, Prof. Anton Mayr succeeded in attenuating CVA by over 570 continuous passages in CEF cells (Mayr A and Munz E 1964, Veränderung von Vaccinevirus durch Dauerpassagen in Hühnerembryofibroblasten-Kulturen, Zentralbl. Bakteriol. 195, 24-35; Mayr A, Hochstein-Mintzel V, Stickl H 1975, Passage History: Abstammung, Eigenschaften and Verwendung des attenuierten Vaccina-Stammes MVA. Infection 3, 6-14). As part of the early development of MVA as a pre-smallpox vaccine, there were clinical trials using MVA-517 (corresponding to the $517^{th}$ passage) in combination with Lister Elstree (Stickl H A 1974, Smallpox vaccination and its consequences: first experiences with the highly attenuated smallpox vaccine "MVA". Prev. Med. 3[1], 97-101; Stickl H & Hochstein-Mintzel V 1971, Intracutaneous smallpox vaccination with a weak pathogenic vaccinia virus ("MVA virus"). Munch. Med. Wochenschr. 113, 1149-1153) in subjects at risk for adverse reactions from vaccinia. In 1976, MVA derived from MVA-571 seed stock (corresponding to the $571^{st}$ passage) was registered in Germany as the primer vaccine in a two-stage parenteral smallpox vaccination program. Subsequently, MVA-572 was used in approximately 120,000 Caucasian individuals, the majority children between 1 and 3 years of age, with no reported severe side effects, even though many of the subjects were among the population with high risk of complications associated with vaccinia (Mayr et al. 1978, Der Pockenimpfstamm MVA: Marker, genetische Struktur, Erfahrungen mit der parenteralen Schutzimpfung and Verhalten im abwehrgeschwächten Organismus. Zbl. Bakt. Hyg., I. Abt. Orig. B 167, 375-390). MVA-572 was deposited at the European Collection of Animal Cell Cultures as ECACC V94012707.

Being that many passages were used to attenuate MVA, there are a number of different strains or isolates, depending on the passage number in CEF cells. All MVA strains originate from Dr. Mayr and most are derived from MVA-572 that was used in Germany during the smallpox eradication program, or MVA-575 that was extensively used as a veterinary vaccine. MVA-575 was deposited on Dec. 7, 2000, at the European Collection of Animal Cell Cultures (ECACC) with the deposition number V00120707.

By serial propagation (more than 570 passages) of the CVA on primary chicken embryo fibroblasts, the attenuated CVA-virus MVA (modified vaccinia virus Ankara) was obtained.

MVA was further passaged by Bavarian Nordic and is designated MVA-BN, corresponding to passage 583. MVA as well as MVA-BN, lacks approximately 13% (24.5 kb from six regions) of the genome compared with ancestral CVA virus (Meisinger-Henschel et al., 2007, Genomic sequence of chorioallantois vaccinia virus Ankara, the ancestor of modified vaccinia virus Ankara. J. Gen. Virol. 88, 3249-3259). The deletions affect a number of virulence and host range genes, as well as the gene for type A inclusion bodies. A sample of MVA-BN was deposited on Aug. 30, 2000 at the European Collection of Cell Cultures (ECACC) with the deposition number V00083008.

MVA-BN can attach to and enter human cells where virally-encoded genes are expressed very efficiently. However, assembly and release of progeny virus does not occur. Preparations of MVA-BN and derivatives have been administered to many types of animals, and to more than 2000 human subjects, including immunodeficient individuals. All vaccinations have proven to be generally safe and well tolerated.

The perception from many different publications is that all MVA strains are the same and represent a highly attenuated, safe, live viral vector. However, preclinical tests have revealed that MVA-BN demonstrates superior attenuation and efficacy compared to other MVA strains (Chaplin P J, Howley P, Meisinger C 2002, Modified Vaccinia Ankara Virus Variant. International Patent Application WO 02/42480). MVA-BN has been shown to have the highest attenuation profile compared to other MVA strains and is safe even in severely immunocompromised animals.

Although MVA exhibits strongly attenuated replication in mammalian cells, its genes are efficiently transcribed and translated, with the block in viral replication being at the level of virus assembly and egress. (Sutter and Moss 1992, Non-replicating vaccinia vector efficiently expresses recombinant genes. Proc. Natl. Acad. Sci. U.S.A 89, 10847-10851; Carroll and Moss 1997, Host range and cytopathogenicity of the highly attenuated MVA strain of vaccinia virus: propagation and generation of recombinant viruses in a nonhuman mammalian cell line. Virology 238, 198-211.) Despite its high attenuation and reduced virulence, in preclinical studies MVA has been shown to elicit both humoral and cellular immune responses to vaccinia virus proteins and the products of genes cloned into the MVA genome (Harrer et al. 2005, Therapeutic Vaccination of HIV-1-infected patients on HAART with recombinant HIV-1 nef-expressing MVA: safety, immunogenicity and influence on viral load during treatment interruption. Antiviral Therapy 10, 285-300; Cosma et al. 2003, Therapeutic vaccination with MVA-HIV-1 nef elicits nef-specific T-helper cell responses in chronically HIV-1 infected individuals. Vaccine 22(1), 21-29; Di Nicola et al. 2003, Clinical protocol. Immunization of patients with malignant melanoma with autologous CD34(+) cell-derived dendritic cells transduced ex vivo with a recombinant replication-deficient vaccinia vector encoding the human tyrosinase gene: a phase I trial. Hum. Gene Ther., 14[14], 1347-1360; Di Nicola et al. 2004, Boosting T cell-mediated immunity to tyrosinase by vaccinia virus-transduced, CD34 (+)-derived dendritic cell vaccination: a phase I trial in metastatic melanoma. Clin. Cancer Res. 10[16], 5381-5390.)

MVA-BN and recombinant MVA-BN-based vaccines can be generated, passaged, produced and manufactured in CEF cells cultured in serum-free medium. Many recombinant MVA-BN variants have been characterized for preclinical and clinical development. No differences in terms of the attenuation (lack of replication in human cell lines) or safety (preclinical toxicity or clinical studies) have been observed between MVA-BN, the viral vector backbone, and the various recombinant MVA-based vaccines.

The safety and immunogenicity of MVA-BN and recombinant MVA-BN vaccines have been demonstrated in more than 15 completed or on-going clinical trials in healthy subjects, patients diagnosed with atopic dermatitis, HIV infected patients, and cancer (melanoma) patients.

A recombinant MVA expressing influenza virus hemagglutinin (HA) and nucleoprotein (NP) genes was generated and tested in mice. Antibody and CTL responses were generated and the mice were protected against a lethal challenge of influenza virus (Sutter et al. 1994, Vaccine 194, 1032-1040).

An H5N1 vaccine candidate based on the replication-deficient modified vaccinia virus Ankara (MVA) has been generated and tested in mice (Kreijtz et al. 2007, Journal of Infectious Diseases 195, 1598-1606). The MVA expressed the hemagglutinin (HA) gene from influenza virus A/Hongkong/156/97 (MVAHA-HK/97) or A/Nietnam/1194/04 (MVA-HA-VN/04). Id. The mice were then challenged with 3 antigenically distinct strains of H5N1 influenza viruses: A/Hongkong/156/97, A/Nietnam/1194/04, and A/Indonesia/5/05. Id. A 2-dose immunization regimen induced strong antibody responses that partially cross-reacted with heterologous H5N1 strains. Id. The elicited antibody responses correlated with protection against challenge infection with homologous and heterologous influenza virus strains. Id. Similarly, immunization of macaques with MVA-HA-VN/04 induced (cross-reactive) antibodies and prevented virus replication in the upper and lower respiratory tract and the development of severe necrotizing bronchointerstitial pneumonia (Kreijtz et al. 2009, Vaccine 27, 6296-6299).

A vaccinia-based influenza vaccine, which expresses the immune stimulatory cytokine IL-15, the hemagglutinin, neuraminidase, and nucleoprotein derived from the H5N1 influenza virus A/Nietnam/1203/2004, and the matrix proteins M1 and M2 from the H5N1 A/CK/Indonesia/PA/2003 virus on the backbone of a currently licensed smallpox vaccine, was generated (Poon et al. 2009, Journal of Immunology 182, 3063-3071). The vaccine induced cross-neutralizing antibodies and cellular immune responses in vaccinated mice and conferred sterile cross-Glade protection when challenged with an H5N1 virus of a different Glade. Id.

There are number of problems with the currently marketed seasonal flu vaccines. First, yearly adaptation of strains is required according to forecast by WHO, with a short window to immunize target populations. This is especially true for young children, who require two doses for priming. The standard vaccine, killed trivalent-split/subunit (TIV), is poorly priming in children. That is, it induces no or only weak immunity in naïve individuals, which is suspected to compromise induction of cross-immunity to other strains/subtypes and thus being counterproductive to the immune constitution (Bodewes et al. 2009, Lancet 9, 784-788; Bodewes et al. 2009, PlosOne 9, e5538:1-9)

It is also poorly immunogenic in elderly persons. An adjuvanted TIV induces stronger immunity in children and elderly, but the impact on immune constitution in young children is unknown. Another vaccine, cold-adapted live-attenuated (CAIV) is a good priming vaccine in naïve subjects, but is a poorly boosting vaccine in pre-immune subjects, e.g. adults. Due to safety concerns in young children, asthmatic attacks and increased incidence of hospitalization after vaccination, it is licensed only for healthy children over two years of age and for asthmatic children over five years of age.

Based on the above, there is a need in the art for flu vaccines both for pandemic flu and for seasonal flu, particularly in young children, and providing increased protection for older children and adults. The current invention fulfills this need and provides means and methods for combating flu by modified vaccinia virus Ankara (MVA)-based vectors as vaccines. The MVA-based vectors build a platform that allows fast and efficient production of flu vaccines that are preferably envisaged not to be subject of adaptation on a yearly basis because of the multivalency of the vaccine and its potential cross-protection. This is achieved by the choice of the external and internal influenza virus antigens and/or an antigenic determinant or epitope thereof offered to the immune system by vaccination.

BRIEF SUMMARY OF THE INVENTION

With the aim of providing influenza vaccines for combating pandemic flu as well as seasonal flu, the present invention provides the following aspects characterized by the following items:

(1) A modified vaccinia virus Ankara (MVA) expressing at least two external influenza virus antigens and/or an epitope of one or more of the at least two antigens and at least two internal influenza virus antigens and/or an epitope of one or more of the at least two antigens, wherein the genes encoding the antigens and/or epitope(s) thereof are inserted into at least two MVA insertion sites.

(2) The MVA virus of item 1, wherein the MVA virus expresses at least 3 external influenza virus antigens and/or an epitope of one or more of the at least 3 antigens and at least 2 internal influenza virus antigens and/or an epitope of one or more of the at least 2 antigens.

(3) The MVA virus of item 1 or 2, wherein the MVA virus expresses at least 3 external influenza virus antigens and/or an epitope of one or more of the at least 3 antigens and at least 3 internal influenza virus antigens and/or an epitope of one or more of the at least 3 antigens.

(4) The MVA virus of any one of items 1-3, wherein the MVA virus expresses at least 6 external influenza virus antigens and/or an epitope of one or more of the at least 6 antigens and at least 3 internal influenza virus antigens and/or an epitope of one or more of the at least 3 antigens.

(5) The MVA virus of any one of items 1-4, wherein the at least two external antigens and/or the epitope(s) of one or more of the at least two antigens are selected from the group consisting of HA, NA, and M2.

(6) The MVA virus of any one of items 1-5, wherein the external antigens are
HA, NA, and M2 and/or an epitope of one or more of said antigens.

(7) The MVA virus of any one of items 1-6, wherein the at least two internal antigens and/or the epitope(s) of one or more of the at least two antigens are selected from the group consisting of PB1, NP, and M1.

(8) The MVA virus of any one of item 1-7, wherein the internal antigens are
PB1, NP, and M1 and/or an epitope of one or more of said antigens.

(9) The MVA of item 8, wherein the internal antigens PB1, NP, and M1 and/or the epitope(s) of one or more of said antigens are expressed as fusion protein.

(10) The MVA virus of any one of items 1-9, wherein the MVA virus expresses four different HA proteins and/or an epitope of one or more of said proteins.

(11) The MVA virus of item 10, wherein the HA proteins are H2, H5, H7, and H9 and/or an epitope of one or more of said proteins.

(12) The MVA virus of item 10, wherein the HA proteins are H1, H3, and two B-type HA proteins and/or an epitope of one or more of said proteins.

(13) The MVA virus of any one of items 1-12, wherein the MVA virus used for generating the recombinant virus is MVA-BN or a variant of MVA-BN.

(14) The MVA virus of any one of items 1-13, wherein the expression of the influenza virus antigens is under the control of more than one poxvirus promoter.

(15) The MVA virus of any one of items 1-14, wherein the genes are inserted into at least two intergenic regions of the MVA genome.

(16) The MVA virus of item 15, wherein the intergenic regions are selected from IGR 44/45, IGR 64/65, IGR 88/89, and IGR 148/149 of the MVA virus.

(17) A vaccine or pharmaceutical composition comprising the MVA virus of any one of items 1-16 and a pharmaceutically acceptable carrier, diluent and/or additive.

(18) Use of the MVA of any one of items 1-16 for the preparation of a medicament or vaccine.

(19) A method for treating a subject, including a human, comprising administering the MVA of any one of items 1-16 and/or the vaccine or pharmaceutical composition of item 17 to the subject, including the human.

(20) The MVA virus of any one of items 1-16, the vaccine or pharmaceutical composition of item 17, the use of item 18 and/or method of item 19 for use in the treatment or prevention of influenza of a subject, including a human.

(21) The method of item 19 or 20 and/or the MVA virus, vaccine or pharmaceutical composition and/or use of item 20, wherein the subject, including the human, is more than 2 years of age.

(22) The method of item 19 or 20 and/or the MVA virus, vaccine or pharmaceutical composition and/or use of item 20, wherein the subject, including the human, is less than 2 years of age.

(23) The method of any one of items 19-22 and/or the MVA virus, vaccine or pharmaceutical composition and/or use of any one of items 20-22, wherein the MVA virus and/or vaccine or pharmaceutical composition is administered in a single or in multiple administrations to a naïve subject.

(24) The method of any one of items 19-23 and/or the MVA virus, vaccine or pharmaceutical composition and/or use of any one of items 20-23, wherein the subject, including the human, is immune-compromised.

(25) The method of any one of items 19-24 and/or the MVA virus, vaccine or pharmaceutical composition and/or use of any one of items 20-24, wherein the MVA virus and/or vaccine or pharmaceutical composition is administered in a therapeutically effective amount in a first inoculation ("priming inoculation") and in a second inoculation ("boosting inoculation").

(26) A kit for prime/boost immunization comprising the MVA virus of any one of items 1-16 and/or the vaccine or pharmaceutical composition of item 17 for a first inoculation ("priming inoculation") in a first vial/container and for a second inoculation ("boosting inoculation") in a second vial/container.

(27) A kit comprising one or multiple vials of the MVA virus of any one of items 1-16 and/or the vaccine or pharmaceutical composition of item 17 and instructions for the administration of the virus to a subject.

(28) A cell comprising the MVA virus of any one of items 1-16.

MVA is particularly suited as vector system. Its potency to be effective in inducing both humoral and cellular immune responses in a short period of time after vaccination against, for example, small pox virus has been demonstrated. Its safety has been established. Its potency to even induce an immune response in immune-compromised subjects is known (for example, a highly attenuated (HA) MVA such as MVA-BN for use as a HIV vaccine).

However, apart from the advantages that HA-MVA does have for use as a vaccine against flu, the greatest challenge for a flu vaccine is the choice of the flu antigens that are offered to a subject's immune system. In fact, a vaccine which avoids the requirement for seasonal reformulation would make the six month lead time needed to produce the vaccines in large quantities not applicable and vaccination coverage easier particularly for influenza-naïve children, which have to be vaccinated twice initially in general. Current flu vaccines use specific proteins from the influenza virus (mostly hemagglutinin HA and neuraminidase NA) to stimulate protective immune responses. However, there is considerable seasonal variation in these proteins, which means a vaccine produced one year may be ineffective the next. New vaccines therefore need to be produced every year to keep up with this variation, and different vaccines will be needed if a new flu pandemic occurs.

The present inventors have instead used a combination of external and internal flu antigens. According to textbook knowledge (Fields: Virology 2007, $5^{th}$ edition, Vol. 2) external antigens are antigens from the virion surface and internal antigens are antigens from the interior of the viral particle. PB1 (subunit of the viral polymerase), NP (nucleoprotein) and M1 (matrix protein) are counting to internal influenza antigens and are preferably used as internal antigens according to the present invention, and HA (hemagglutinin), NA (neuraminidase) and M2 (matrix protein) are external antigens of influenza virus (Fields: Virology 2007, $5^{th}$ edition, Vol. 2, 1648, right column, section "Virion Structur", $2^{nd}$ sentence, or 1649, FIG. 47.2) and are preferably used as external antigens according to the present invention. The inventors' choice of a combination of external and internal flu antigens thus serves as a basis for an improved flu vaccine.

The internal proteins, which are conserved in avian flu viruses as well as in those causing seasonal human flu, are expressed by a viral vector (MVA), which acts as an adjuvant, stimulating not only B-cell responses but also powerful T-cell responses. Particularly the latter type of responses is increasingly thought to be important in providing immunity to the flu virus. The potency of MVA to induce significant heterosubtypic T cell responses has recently been corroborated by a study of Bertoud et al. 2011 (Potent CD81 T-Cell Immunogenicity in Humans of a Novel Heterosubtypic Influenza A Vaccine, MVA-NP+M1. Clin. Infect. Dis. 52, 1-7). However, while Bertroud et al. could demonstrate a heterosubtypic T cell response, these authors could not achieve their goal for an influenza vaccine, since external/surface antigens such as the hemagglutinin were apparently absent in their vaccine.

In addition, the present inventors have foreseen that the vaccine of the present invention, if it is primarily applied as pandemic (pan) flu vaccine, expresses preferably four different HA proteins (H2, H5, H7 and H9) or preferably H1 and H3 and two B-type HA proteins when preferably applied as seasonal flu vaccine.

Broad induction of hetero-subtypic responses combined with three H-clades (Russell et al. 2004, Virology 325, 287-296) in the case of the pandemic (pan) influenza vaccine are envisaged to render a substantial prospective potential of this vaccine such that subtypes not covered by the vaccine would be covered indirectly by the breadth of the immune response induced. In fact, an approach using solely internal antigens as described by Schneider 2010 (BIT Life Science, $2^{nd}$ Annual World Vaccine Congress) was regarded as an insufficient concept, if external/surface antigens such as the hemagglutinin are not included.

BRIEF DESCRIPTION OF THE DRAWINGS

The invention is more fully understood with reference to the drawings, in which:
FIG. 5 depicts MVA-PanFlu.
FIG. 7 depicts pBN418.

DETAILED DESCRIPTION OF THE INVENTION

Figure 1:
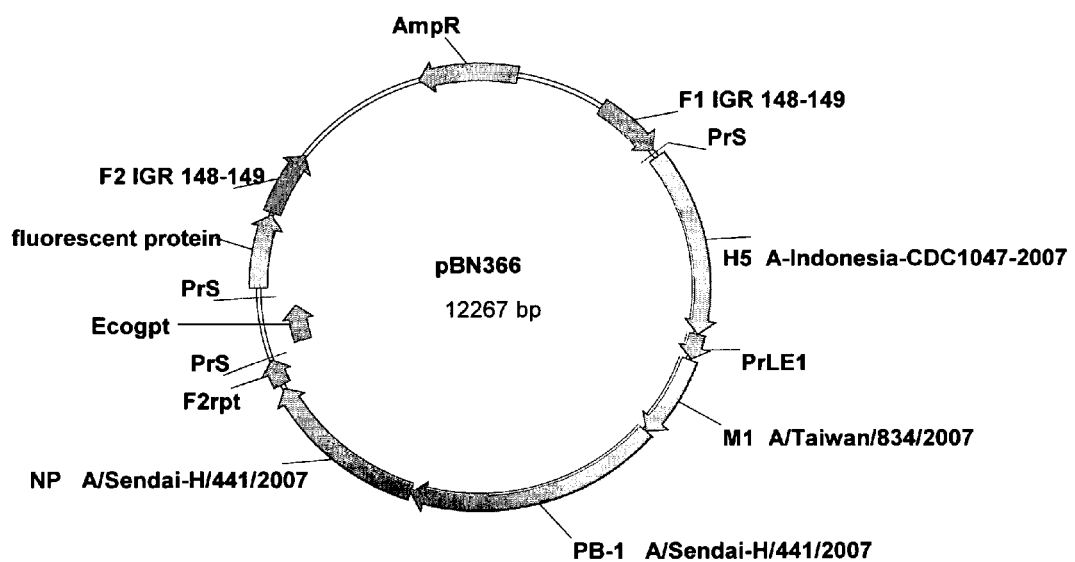
FIG. 1 depicts pBN366.

In order to meet the challenges of next generation influenza vaccines, the present inventors have developed an MVA-based influenza vaccine that will combine both external and internal viral proteins in a viral vector that can be produced in an easily available cell culture system. Neutralizing antibodies to external viral surface proteins play a crucial role in preventing establishment of infection, whereas cytotoxic T lymphocytes to internal viral proteins will clear cells that are already infected. Accordingly, the present inventors regarded it as appropriate to include both external and internal viral proteins in a vaccine construct.

The vaccine of the present invention is envisaged to be a "universal vaccine" both for seasonal and pandemic flu which would be able to protect against different influenza strains. For this purpose, PB1 (subunit of the viral polymerase), NP (nucleoprotein) and/or M1 (matrix protein) are preferably used as internal antigens and HA (hemagglutinin), NA (neuraminidase) and/or M2 (matrix protein-2) are preferably used as external antigens. In addition, the vaccine comprises preferably four different HA proteins (H2, H5, H7 and H9) (pandemic or pre-pandemic vaccine) or H1 and H3 and two B-type HA proteins (seasonal vaccine). "Universal vaccine" when used herein means in particular that the vaccine of the present invention is "universal for the range of H-clades", i.e., the vaccine is envisaged to confer protection against the H-clades H2, H5, H7 and/or H9 or H1, H3 and/or two B-type HA-proteins, in particular from the Yamagata and Victoria line, respectively, and/or cross-protection against one or more H-clades different from H2, H5, H7 and/or H9 or H1, H3 and/or two B-type HA-proteins, in particular frp, the Yamagata and Victoria line, respectively, such as those described in Russell et al. 2004, Virology 325: 287-296; see herein below.

MVA Strains

The present invention encompasses a modified vaccinia virus ankara (MVA) comprising influenza virus genes and MVA-based vaccines. Accordingly, the present invention also encompasses recombinant MVAs. The MVA backbone can preferably be MVA 572 or MVA 575 or MVA-BN as deposited with the ECACC under deposit number V00083008.

MVA-based vaccines are advantageous for several reasons. For example, the preferred strain MVA strain MVA-BN grows well in primary Chicken Embryo Fibroblast (CEF) cells and does not replicate in human cells as described in more detail herein. In human cells, the viral genes are expressed, but no infectious virus is produced. The restricted host range of MVA-BN may explain the non-virulent phenotype observed in vivo in a wide range of mammalian species including humans.

Some key features of MVA-BN that make this a promising vaccine vector include:

- MVA-BN fails to replicate in human cell lines or mammalians, even in severely immune suppressed mice.
- MVA-BN has been shown to be safe in numerous toxicity studies, including repeated toxicity exposure in rabbits as well as peri- and post-natal teratology studies in pregnant dams and pups, and MVA-BN has been shown to be rapidly cleared (within 48 hours post vaccination) from rabbits in a biodistribution study.
- MVA-BN can be used in homologous prime-boost regimes even in the presence of a pre-existing immunity to the viral vector.
- More than 2000 people have been safely vaccinated with MVA-BN or recombinant MVA-based vaccines, including healthy subjects, Human Immunodeficiency Virus (HIV) infected people (CD4 cells=>200 µl) and people diagnosed with Atopic Dermatitis (AD).
- MVA-BN is capable of providing immediate protection in an animal model of mousepox (i.e., conferring protection against concomitant infection), and/or post-exposure protection (i.e., conferring protection after an infection has occurred).

MVA-mBN210 is an example of a highly attenuated modified vaccinia virus Ankara ("HA-MVA"). When used herein, the term "HA-MVA" is interchangeably used with the term "MVA-BN".

According to the present invention, an "HA-MVA" (or "MVA-BN") virus is an MVA virus having the following properties:

- An HA-MVA virus fails to reproductively replicate in vitro in human cell lines (such as HaCaT, 143B, 293 and HeLa).
- An HA-MVA virus fails to reproductively replicate in vivo in humans and mice, even in severely immune suppressed mice.
- An HA-MVA virus has a virus amplification ratio at least two fold less than MVA-575 in Hela cells and HaCaT cell lines.
- An HA-MVA virus has the capacity to reproductively replicate in chicken embryo fibroblast cells.

When used herein "highly attenuated" means that an MVA has the capability of reproductive replication in chicken embryo fibroblasts (CEF), but no capability of reproductive replication in the human keratinocyte cell line HaCaT, the human bone osteosarcoma cell line 143B, the human embryo kidney cell line 293, and the human cervix adenocarcinoma cell line HeLa.

The term "fails to reproductively replicate" applies to a virus that has a virus amplification ratio at 4 days after infection of less than 1 using the assays described in WO 02/42480, which assays are hereby incorporated by reference.

Preferably, an HA-MVA has a virus amplification ratio at least three fold less than MVA-575 in Hela cells and HaCaT cell lines. The HA-MVA virus can be derived by the further passage of a modified vaccinia virus Ankara (MVA), such as MVA-572 or MVA-575.

In a preferred embodiment, the HA-MVA virus has an amplification ratio of greater than 500 in CEF cells.

HA-MVA viruses include recombinant viruses derived from HA-MVA as well as MVA-BN and recombinant viruses derived from MVA-BN, for example, by insertion of a heterologous gene under the control of a poxvirus promoter. A sample of MVA-BN was deposited with the ECACC under deposit number V00083008.

When used herein "a derivative" or "variant" of HA-MVA has preferably the same properties as HA-MVA, i.e., the capability of reproductive replication in chicken embryo fibroblasts (CEF), but no capability of reproductive replication in the human keratinocyte cell line HaCaT, the human bone osteosarcoma cell line 143B, and the human cervix adenocarcinoma cell line HeLa. As indicated above, tests and assay for these properties of MVA are described in WO 02/42480 (incorporated by reference).

"Derivatives" of MVA-BN refer to viruses exhibiting essentially the same replication characteristics as MVA-BN, but exhibiting differences in one or more parts of their genomes. MVA-mBN210 is a derivative of MVA-BN.

In preferred embodiments, the invention encompasses a HA-MVA virus encoding multiple external and/or internal influenza virus antigens. In a preferred embodiment, the HA-MVA virus is a recombinant HA-MVA derived from MVA-BN, i.e, the MVA virus used for generating the recombinant virus is, preferably, MVA-BN or a variant having the same growth characteristics—see above. The influenza virus genes can be cloned into MVA-BN or a variant thereof. In a particularly preferred embodiment, the virus is MVA-mBN210 (see FIG. 5) or MVA-mBN242 (see FIG. 8).

The propagation of a MVA, for example, HA-MVA in culture can lead to mutations in the genome of the MVA such as HA-MVA. By using the appropriate selection procedures (i.e., propagation on particular cell lines), the desired phenotype can be maintained, while allowing mutations that do not affect these properties. Methods for propagating MVA on various cell lines are well known in the art.

The additions of mutagens to the media in which the viruses are grown can facilitate the generation of mutations in the genome of MVA, such as a HA-MVA virus. Similarly, PCR and other molecular techniques can be used to introduce mutations into the genome of MVA, for example, HA-MVA. These mutations can be targeted to non-essential regions of the genome or can be randomly generated.

In one embodiment, the recombinant MVA is at a concentration of $10^7 TCID_{50}$/ml or greater. Preferably, the recombinant MVA is produced from infected cells, preferably CEF, at a concentration of $10^7$ $TCID_{50}$/ml or greater.

In a preferred embodiment, the recombinant MVA is grown at a temperature of 30° C., preferably in serum-free media (e.g. VP-SFM™). In a preferred embodiment, the recombinant MVA is grown at a pH of less than 5.5, preferably at pH 5.2.

Influenza Virus Genes

Influenza virus type A is a genus of a family of viruses called Orthomyxoviridae in virus classification. Influenza virus type A has only one species in it; that species is called "Influenza A virus". Influenza A virus causes "avian influenza" (also known as bird flu, avian flu, Influenza virus A flu, type A flu, or genus A flu), but also human influenza, porcine influenza or equine influenza. Birds are its major animal reservoir, but influenza A viruses may infect several species of mammals. Influenza virus type B is another genus of a family of viruses called Orthomyxoviridae. Influenza virus type B has only one species in it; that species is called "Influenza B virus".

The influenza virus antigens or antigenic determinants or epitopes thereof are preferably from multiple influenza virus strains. "Multiple" in this context means the influenza virus genes/antigens/epitopes as applied in the vectors and vaccines of the present invention are from different influenza virus strains. For example, an M2 gene may be from a first influenza virus strain, while the PB-2 gene may be from a second influenza virus strain which differs from the first strain. However, it is nevertheless also preferred that one or more of the influenza virus genes/antigens/epitopes as applied in the vectors and vaccines of the present invention are from the same influenza virus strain.

As used herein, the terms "epitope" or "antigenic determinant" are used synonymously to refer to a short peptide sequence of a reference influenza antigen as described herein, that is specifically recognized or specifically bound by a component of the immune system. Generally, antigens are recognized in the context of an MHC/HLA molecule to which they are bound on an antigen presenting cell. "Eptitope" or "antigenic determinant" refer to an amino acid stretch or peptide or fragment of an antigen or of an antigenic polypeptide or protein, which is sufficiently long to induce a specific immune response against the antigen from which the epitope or antigenic determinant is derived. Thus, epitopes are short stretches of peptides which are parts of an antigen that are recognized by the immune system and which are still capable of eliciting an immune response in a vaccinated animal including a human. An epitope or antigenic determinant is, thus, a fragment, portion or segment of the antigen or antigenic polypeptide.

The terms "peptide" or "amino acid sequence" refer to an oligopeptide, peptide, a fragment of a polypeptide or protein sequence and to naturally occurring or synthetic molecules. A polypeptide "fragment", "portion", or "segment" is a stretch of amino acid residues of at least about 5 amino acids, preferably at least about 7 amino acids, more preferably at least about 9 amino acids and most preferably at least about 17 or 20 or more amino acids. The peptide preferably is not greater than about 200 amino acids, more preferably less than 150 amino acids and most preferably less than 100 amino acids. Preferably the peptide is from about 5 to about 200 amino acids. To be immunogenic, i.e., serving as epitope, any peptide or polypeptide must have sufficient length to display biological and/or immunological activity. Preferably, a polypeptide "fragment", "portion" or "segment" as described herein serves as an epitope or antigenic determinant.

As used herein, "antigenic determinant" or "epitope", when not expressly mentioned, are always encompassed by the term "antigen".

The recombinant MVA can comprise any and all combinations of the following influenza virus genes or fragments or mutants thereof: hemagglutinin HA, neuraminidase NA, matrix protein M2, M1, nucleoprotein NP, polymerase basic PB1, PB2, PB1-F2, polymerase acid PA, nonstructural protein NS1, and NS2 of influenza A and/or B. Said fragments or mutants are preferably still capable of inducing an immune response including a humoral and/or cellular immune response such as the production of antibodies, preferably neutralizing antibodies or the induction of a cytolytic immune response. In a particularly preferred embodiment, the recombinant MVA comprises 2, 3, 4, 5, 6, or more HA genes and at least one PB1 gene.

In one embodiment, the recombinant MVA comprises one or more influenza virus genes encoding a mutated or truncated version of the encoded influenza virus protein, for example, a nonstructural NS1 or NS2 protein.

In a preferred embodiment, the recombinant MVA comprises internal and external genes of influenza virus. Preferably, the recombinant MVA comprises at least 2, 3, 4, or 5, or 6 internal genes and at least 2, 3, 4, 5, or 6 external genes. More preferably, the recombinant MVA comprises at least 2 or 3, 4, or 5, or 6 different internal genes and at least 2, 3, 4, 5, or 6 different external genes. In a particularly preferred embodiment, the recombinant MVA comprises 2, 3, 4, 5, 6, or more different HA genes and at least one PB1 gene.

External antigens are important for early neutralization and blocking of virus entry and fusion; internal antigens are important for the T-cell response especially for CTLs. Both antigen types can induce cross-reactive and cross-protective immunity, which is important in the context of flu given the many strains of potential interest or arising by mutating viruses.

The internal antigens are expected to improve cross-reactivity because they are well conserved across all influenza A and even B viruses. It is envisaged that the internal antigens induce a CTL response, since antibodies against these antigens, though useful, do not provide a sufficient protection. CTL responses alone will in most cases not be protective by themselves but they contribute to protection and could mitigate disease or prevent death while not protecting against disease in general.

In contrast to other known constructs which are intended to induce heterosubtypic CTL responses, the present inventors included an open reading frame (ORF) coding for the PB1 subunit of the viral polymerase in addition to the often used M1 (matrix protein) and NP (nucleoprotein) antigens. PB1 has been shown to be a preferred target of the hetero-subtypic CTL responses in humans across various MHC haplotypes (Assarsson et al. 2008, J. Virol. 82, 12241-51). Moreover, it seems that the recent vH1N1 (swine flu) already confirms the present inventors' decision to preferably use PB1, since the PB1 gene was the only gene in vH1N1 derived from humans. Therefore it could be of particular importance for the virus.

The internal antigens and/or epitope(s) of PB1, M1 and/or NP are, preferably, expressed as fusion protein.

In one embodiment, the recombinant MVA comprises 4, 5, 6, 7, 8, 9, 10, 11, 12, 13, 14, 15, or more influenza virus genes. "Influenza virus genes" when used herein means preferably influenza virus open reading frames. In a preferred embodiment, the recombinant MVA comprises 9 influenza virus genes. Indeed, the present invention envisages polyvalent vaccines in order to cover all 16 hemagglutinins (subtypes) by, for example, 3 to 4 vaccines and by this build a pandemic library. The MVA-based vaccine is thus a flexible and powerful tool to combat future outbreaks of new influenza viruses.

In one embodiment, the recombinant MVA comprises at least 4 different HA genes, one NA gene, one M2 gene, one M1 gene, one NP gene, and one PB1 gene. M1 is a protein that binds to the viral RNA and constitutes the inner shell of the viral envelope. M2 is a protein that helps in uncoating the virus exposing its contents (the eight RNA segments) to the cytoplasm of the host cell. The M2 transmembrane protein is an ion channel required for efficient infection (Robert B. Couch, Orthomyxoviruses, Baron S. (ed.) 1996 in Medical Microbiology, Fourth Edition, The University of Texas Medical Branch at Galveston, ISBN 0-9631172-1-1).

The recombinant MVA can comprise at least 2, 3, 4, 5, 6, 7, 8, or more copies of a particular gene. Specifically, in order to cover the influenza virus subtype that might cause a pandemic in the future, a polyvalent vaccine covering several—at least two—subtypes of influenza A is of value to immunize subjects pre-pandemically simultaneously against several potential pandemic candidate viruses (general use prophylaxis, GUP) or to stockpile the vaccine to be used at the time a pandemic is declared, for ring vaccination (e.g. according to modeling) or for post-exposure prophylaxis (PEP).

Up to now H3N2, H1N1 and at least one type B co-circulated as seasonal flu viruses. H1N1, co-circulating since 1977, was replaced by vH1N1 (swine flu) as the prevalent H1N1 subtype and will most likely disappear. The future of H3N2 is open for the moment and it might disappear in the near future as well. Since 1997 a re-appearance of Influenza Virus B (IVB) from the lineage B-Victoria besides the B-Yamagata has occurred and since then viruses from both B-lineages are co-circulating.

A polyvalent vectored vaccine would circumvent the need to mix several monovalent vaccines to achieve a polyvalent vaccine taking into account the co-circulation of several seasonal viruses. This can be achieved in one MVA-based construct as provided by the present invention, which is polyvalent by its nature. This facilitates the production pathway in contrast to the established approach.

Preferably, the recombinant MVA comprises 2, 3, 4, 5, 6, 7, 8, or more HA genes. In a preferred embodiment, the recombinant MVA comprises 4 different HA genes. In another preferred embodiment, the recombinant MVA comprises at least two different B-type HA proteins such as from the Victoria or Yamagata line Preferably, the influenza virus gene is a full-length gene. In other embodiments, a gene fragment comprises 30%, 40%, 50%, 60%, 70%, 75%, 80%, 85%, 90%, 95%, 97%, 98%, or 99% of a full-length gene.

Preferably, the size of the inserted influenza virus gene is about 700, 1000, 1400, 1500, 1700, or 2300 nucleotides. Particularly preferred is a recombinant MVA comprising at least 5,000, 6,000, 7,000, 8,000, 9,000, 10,000, 11,000, 12,000, 13,000, 14,000, or 15,000 nucleotides of influenza virus gene sequences. Especially preferred is a recombinant MVA comprising at least 13,700 nucleotides of influenza virus gene sequences, for example, inserted into 2, 3, 4, 5, or 6 different sites in the MVA genome, and controlled by 5, 6, 7, 8, or 9 promoters.

In a preferred embodiment, the 4 different HA genes naturally have as high as 70% identity at the nucleotide sequence level. In a preferred embodiment, the 4 different HA genes have no more than 64% identity at the nucleotide sequence level after these genes have been optimized for expression in human cells by altering the nucleic acid sequence with mutations that do not affect the amino acid sequence. In a preferred embodiment, the 4 different HA genes have between 52% and 64% identity at the nucleic acid level.

The determination of percent identity between two sequences is accomplished using the mathematical algorithm of Karlin and Altschul 1993, PNAS 90, 5873-5877. Such an algorithm is incorporated into the BLASTN and BLASTP programs of Altschul et al. 1990, J. Mol. Biol. 215, 403-410. BLAST nucleotide searches are performed with the BLASTN program, preferably with score=100, word length=12. BLAST protein searches are preferably performed with the BLASTP program, score=50, wordlength=3. To obtain gapped alignments for comparative purposes, Gapped BLAST is utilized as described in Altschul et al. 1997, Nucleic Acids Res. 25, 3389-3402. When utilizing BLAST and Gapped BLAST programs, the default parameters of the respective programs are preferably used.

Preferably, the HA genes are from different HA subtypes, i.e., H1-H16. In one embodiment, the recombinant MVA comprises HA genes of H2, H5, H7, and/or H9 H types. In one embodiment, the recombinant MVA comprises HA genes of H3, vH1, and two B-type HA genes, in particular B-Bris and B-Yam HA subtypes.

By integration of H9, H5, H2, H7 HAs, four subtypes with proven infections in humans were integrated into an HA-MVA of the present invention. By this three of the 4 H-clades (Russell et al. 2004, Virology 325, 287-296) are covered and it is envisaged to close the gaps of not-included H clades. Since H3 (the fourth H-Glade) circulates seasonally anyway, the best case scenario would be that this clade is covered to some extent by cross-protection. Although one might expect less vaccine efficacy against hetero-subtypic strains, even a less effective vaccine that induces an immune reaction is sufficient to avoid severe disease or death and to possibly reduce transmission that would be of great value, since modeling revealed that a low-efficacious vaccine immediately available would be of higher value than a highly efficacious vaccine only available with big delay. This can preferably be achieved by the vaccine of the present invention.

In a further preferred embodiment, the recombinant MVA comprises a gene encoding the HA, NA and/or M2 antigen(s) and/or epitope(s).

Preferably the HA genes are from different HA clades as defined in Russell et al. 2004, Virology 325, 287-296, i.e., H1 (H1, H2, H5, H6, H11, H13, H16), H9 (H8, H9, H12), H3 (H3, H4, H14), or H7 (H7, H10, H15) clades. Preferably, the recombinant MVA comprises HA genes of 2, 3, or all 4 HA clades. In a preferred embodiment, the recombinant MVA comprises HA genes of H1, H3, H7, and/or H9 clades.

Particularly preferred HA genes are H5 A-Indonesia-CDC1047-2007; H2 A-Wigeon-Norway 10 1783-2006; H9 A-Chicken-Guangddong-GZ02-2008; H7 A-Duck-Mongolia-720-2007, vH1 A-California/7/2009; H3 A-Perth-16-2009; B-Brisbane-03-2007; B-Brisbane-03-2007; and B-Florida-04-2006.

Particularly preferred NA genes are N1 A-Indonesia-CDC1047-2007. Particularly preferred M2 genes are M2 A-Hong Kong-2652-2006. Particularly preferred M1 genes are M1 A-Taiwan-843-2007. Particularly preferred NP genes are NP A-Sendai-H-441-2007. Particularly preferred PB1 genes are PB1 A-Sendai-H-441-2007.

Preferably, the nucleotide sequence of the HA genes in an MVA construct are altered to reduce the % A) identity between any two HA genes to less than 65%. For example, the nucleotide sequence of the H2 and H5 genes can be altered to reduce the nucleic acid identity between these genes from 70% to 64%. Preferably, conservative mutations are used that do not alter the amino acid sequence and/or that use codons preferred in human cells.

Preferably, the recombinant MVA expresses a functional NA protein. The functional NA protein can promote a better yield of viruses during the production of the recombinant viruses. Accordingly, in order to have MVA express a functional NA protein the gene was put into a separate insertion site—either into a different intergenic region or as a separate transcriptional unit under control of a separate promoter—and not as part of a fusion protein. Beyond this aspect, the neuraminidase preferably acts also as an antigen to increase the breadth of the immune response.

Although less preferred, the influenza sequences may not need to be present in their entirety in the MVA vector of the present invention. According to the present invention, only full length proteins or only an epitope or epitopes or all possible combinations can be expressed by the recombinant virus, i.e., the recombinant may comprise one or more eptiope(s) of one or more of the antigens. By way of example, the recombinant virus may express a first entire internal antigen, one or more epitope(s) of a second internal antigen, one or more epitope(s) of a first external antigen and a complete second external antigen. Likewise, the recombinant MVA vector may express one or more epitope(s) of a first internal antigen, a second full length internal antigen, one or more epitope(s) of a third internal antigen, a complete first external antigen and one or more epitope(s) of a second external antigen, and so on. Preferred are more than one epitope.

Also, the influenza sequences may be codon optimized in order to be, e.g., better expressed or more stable.

In various preferred embodiments, the recombinant MVA does not comprise a gene encoding IL-15.

Integration Sites into MVA

The invention encompasses recombinant MVAs comprising influenza virus genes incorporated in a variety of insertion sites in the MVA genome. "Variety of insertion sites" means that influenza virus genes encoding external and internal antigens and/or epitopes thereof, respectively, can be inserted into the same or one or more different insertion sites in the MVA genome, with different insertion sites being preferred. Different means that, for example, a first insertion site is not the same as a second insertion site. Details regarding insertion sites and the number of insertion sites are described herein below.

The influenza virus genes can be inserted into the recombinant MVA as separate transcriptional units or as fusion genes, as depicted in the examples. In fact, it is known that MVA that contains up to four highly homologous genes is stable (see WO 03/097846). Accordingly, MVA is suitable to take up highly homologous genes such as hemagglutin genes as described herein.

In one embodiment, the influenza virus genes are inserted into intergenic regions of the MVA. In preferred embodiments, the IGR is selected from IGR07/08, IGR 44/45, IGR 64/65, IGR 88/89, IGR 136/137, and IGR 148/149, wherein IGR44/45, IGR64/65, IGR88/89, and/or IGR 148/149 are, in particular, preferred. In a preferred embodiment, HA genes are inserted into IGR44/45, IGR64/65, IGR88/89, and/or IGR 148/149. Preferably, less than 5, 4, 3, or 2 IGRs of the recombinant MVA comprise influenza virus genes. In a particularly preferred embodiment, the recombinant MVA comprises 3, 4, 5, 6, 7, 8, or more HA genes inserted into 1, 2, 3, or 4 IGRs.

In one embodiment, the influenza virus genes are inserted into naturally occurring deletion sites I, II, III, IV, V, or VI of the MVA. Yet, in another embodiment, it is preferred that the influenza genes are not inserted into naturally occurring deletion site III.

The number of insertion sites of MVA containing influenza virus genes can be 1, 2, 3, 4, 5, 6, 7, or more. In preferred embodiments, the recombinant MVA comprises influenza virus genes inserted into 4, 3, 2, or less insertion sites. Most preferably, 2 or 4 insertion sites are used. Two sites are most preferably used for a seasonal flu vaccine, see, for example, FIG. 8. Namely, two influenza virus genes encoding external antigens are inserted into a first site and the influenza virus genes encoding internal antigens are inserted into a second site (different from the first site). Similarly, four insertion sites are most preferably used for a pandemic or pre-pandemic flu vaccine, see, for example, FIG. 5. Namely, a first HA gene is inserted into a first site, a NA gene and a second HA gene are inserted into a second site, a third HA gene and an M2 gene are inserted into a third site and a fourth HA gene and a M1, PB-1 and NP gene are inserted into a fourth site. The M1, PB-1 and NP genes are preferably expressed as a fusion. It is, however, also preferred that the recombinant MVA comprises at least 6, 7, 8, or 9 genes inserted into 2, 3, or 4 insertion sites.

Preferably, the NA gene is inserted as a separate transcriptional unit into the recombinant MVA. More preferably, the NA gene is inserted into IGR 64/65 or 148/149. The expression of a functional NA protein by the recombinant MVA can promote a better yield of viruses during the production of the recombinant viruses and represents an antigen of influenza virus which can induce "permissive immunity" contributing to protection. Accordingly, it is preferred that the NA gene encodes a functional NA protein.

Preferably, the M1, PB1, and NP genes are inserted as a fusion gene into the recombinant MVA, as depicted in the examples. More preferably, the M1, PB1, and NP genes are inserted into IGR 148/149.

Preferably, the M2 gene is inserted as a separate transcriptional unit into the recombinant MVA. More preferably, the M2 gene is inserted into IGR 88/89.

The recombinant MVA virus can be generated by routine methods known in the art. For example, the MVA virus can be generated by following the procedures set out in the Examples.

Methods to obtain recombinant poxviruses or to insert exogenous coding sequences into a poxyiral genome are well known to the person skilled in the art. For example, methods are described in the following references: Molecular Cloning, A laboratory Manual, Second Edition, by J. Sambrook, E. F. Fritsch and T. Maniatis 2003, Cold Spring Harbor Laboratory Press, describes techniques for standard molecular biology techniques such as cloning of DNA, DNA and RNA isolation, western blot analysis, RT-PCR and PCR amplification techniques. Virology Methods Manual, edited by Brian W J Mahy and Hillar O Kangro 1996, Academic Press, describes techniques for the handling and manipulation of viruses. Molecular Virology: A Practical Approach, edited by A J Davison and R M Elliott 1993, The Practical Approach Series, IRL Press at Oxford University Press, Oxford, Chapter 9, Expression of genes by Vaccinia virus vectors. Current Protocols in Molecular Biology, publisher: John Wiley and Son Inc 1998, Chapter 16, section IV: Expression of proteins in mammalian cells using vaccinia viral vector, describes techniques and know-how for the handling, manipulation and genetic engineering of MVA.

For the generation of recombinant poxviruses according to the present invention, different methods may be applicable. The DNA sequence to be inserted into the virus can be placed into an *E. coli* plasmid construct into which DNA homologous to a section of DNA of the poxvirus has been inserted. Separately, the DNA sequence to be inserted can be ligated to a promoter. The promoter-gene linkage can be positioned in the plasmid construct so that the promoter-gene linkage is flanked on both ends by DNA homologous to a DNA sequence flanking a region of poxyiral DNA containing a non-essential locus. The resulting plasmid construct can be amplified by propagation within *E. coli* bacteria and isolated. The isolated plasmid containing the DNA gene sequence to be inserted can be transfected into a cell culture, e.g., chicken embryo fibroblasts (CEFs), along with infection of this culture by the poxvirus. Recombination between homologous poxyiral DNA in the plasmid and the viral genome, respectively, can generate a poxvirus modified by the presence of foreign DNA sequences.

According to a preferred embodiment, a cell of a suitable cell culture as, e.g., CEF cells, can be infected with a poxvirus. The infected cell can be, subsequently, transfected with a first plasmid vector comprising a foreign gene or genes, preferably under the transcriptional control of a poxvirus expression control element. As explained above, the plasmid vector also comprises sequences capable of directing the insertion of the exogenous sequence into a selected part of the poxyiral genome. Optionally, the plasmid vector also contains a cassette comprising a marker and/or selection gene operably linked to a poxyiral promoter. Suitable marker or selection genes are, e.g., the genes encoding the green fluorescent protein, β-galactosidase, neomycin-phosphoribosyltransferase or other markers. The use of selection or marker cassettes simplifies the identification and isolation of the generated recombinant poxvirus. However, a recombinant poxvirus can also be identified by PCR technology. Subsequently, a further cell can be infected with the recombinant poxvirus obtained as described above and transfected with a second vector comprising a second foreign gene or genes. In case, this gene can be introduced into a different insertion site of the poxyiral genome, the second vector also differs in the poxvirus-homologous sequences directing the integration of the second foreign gene or genes into the genome of the poxvirus. After homologous recombination has occurred, the recombinant virus comprising two or more foreign genes can be isolated. For introducing additional foreign genes into the recombinant virus, the steps of infection and transfection can be repeated by using the recombinant virus isolated in previous steps for infection and by using a further vector comprising a further foreign gene or genes for transfection.

Alternatively, the steps of infection and transfection as described above are interchangeable, i.e., a suitable cell can at first be transfected by the plasmid vector comprising the foreign gene and, then, infected with the poxvirus. As a further alternative, it is also possible to introduce each foreign gene into different viruses, co-infect a cell with all the obtained recombinant viruses and screen for a recombinant including all foreign genes. A third alternative is ligation of DNA genome and foreign sequences in vitro and reconstitution of the recombined vaccinia virus DNA genome using a helper virus. A fourth alternative is homologous recombination in E. coli or another bacterial species between a vaccinia virus genome cloned as a bacterial artificial chromosome (BAC) and a linear foreign sequence flanked with DNA sequences homologous to sequences flanking the desired site of integration in the vaccinia virus genome.

A preferred MVA strain used for generating the recombinant virus has preferably the capability of reproductive replication in chicken embryo fibroblasts (CEF), but no capability of reproductive replication in the human keratinocyte cell line HaCaT, the human bone osteosarcoma cell line 143B, and the human cervix adenocarcinoma cell line HeLa.

Preferably, the MVA backbone strain has the same growth characteristics as the strain a sample of which was deposited with the ECACC under deposit number V00083008.

Also preferred are MVA viruses with a virus amplification ratio at least three fold less than MVA 575 in HeLa and HaCaT cell lines and/or viruses with an amplification ratio of greater than 500 in CEF cells.

Expression of Influenza Virus Genes

In one embodiment, expression of one, more, or all of the influenza virus gene or genes or epitope(s) is under the control of one or more poxvirus promoters, wherein the use of more than one poxvirus promoter is preferred. In preferred embodiments, the poxvirus promoter is a Pr7.5 promoter, a hybrid early/late promoter, a PrS promoter, a synthetic or natural early or late promoter such as one of the promoters described in WO 2010/102822 or in WO 2005/054484, or cowpox virus ATI promoter. Preferably, the pS or pHyb promoter as described in WO 2010/102822 (see FIG. 1b) is used.

An influenza gene(s) can be expressed as a single transcriptional unit. For example, an influenza gene(s) can be operably linked to a vaccinia virus promoter and/or linked to a vaccinia virus transcriptional terminator. In one embodiment, one or more influenza genes are expressed as a fusion protein.

The "transcriptional unit" can be inserted by itself into an insertion site in the MVA genome. The "transcriptional unit" can be inserted with other transcriptional unit(s) into an insertion site in the MVA genome. The "transcriptional unit" is not naturally occurring (i.e., heterologous or exogenous or foreign) in the MVA genome and is capable of transcription in infected cells.

Preferably, the recombinant MVA comprises 3, 4, 5, 6, 7, 8, 9, 10, or more transcriptional units inserted into the MVA genome. In one embodiment, the recombinant MVA stably expresses influenza proteins encoded by 3, 4, 5, 6, 7, 8, 9, 10, or more transcriptional units.

In various embodiments, recombinant MVA comprises 3, 4, 5, 6, 7, 8, 9, 10, or more transcriptional units inserted into the MVA genome at 1, 2, 3, 4, 5, 6, or more insertion sites in the MVA genome.

Vaccines Comprising HA-MVA Viruses

Since the recombinant HA-MVA virus according to the invention is highly replication restricted and, thus, highly attenuated, it is an ideal candidate for the treatment of a wide range of mammals including humans and even immune-compromised humans. Moreover, the production of HA-MVA-based vaccines is more or less independent of existing production capacity for conventional influenza vaccines, since MVA can be conveniently cultured in CEF cells. Thus, the HA-MVA based vaccine of the present invention can be produced in large amounts in a short period of time which can be important in case of a pandemic or a seasonal flu that might have the potential to become pandemic. Furthermore, the MVA vector vaccines of the present invention can deliver multiple influenza virus antigens and thus allows for simultaneous induction of high level humoral and cellular immunity providing the possibility to develop multivalent vaccines. Hence, the present invention also provides a pharmaceutical composition and also a vaccine for inducing an immune response in a living animal body, including a human.

The vaccine preferably comprises HA-MVA viruses in a concentration range of $10^4$ to $10^9$ $TCID_{50}$/ml, preferably in a concentration range of $10^6$ to $5\times10^8$ $TCID_{50}$/ml, more preferably in a concentration range of $10^6$ to $10^8$ $TCID_{50}$/ml, and most preferably in a concentration range of $10^7$ to $10^8$ $TCID_{50}$/ml.

A preferred vaccination dose for humans comprises $10^6$ to $10^9$ $TCID_{50}$, most preferably a dose of $10^6$ $TCID_{50}$ or $10^7$ $TCID_{50}$ or $10^8$ $TCID_{50}$.

The pharmaceutical composition may generally include one or more pharmaceutically acceptable and/or approved additives, carriers and/or diluents, antibiotics, preservatives, adjuvants and/or stabilizers. Such auxiliary substances can be water, saline, glycerol, ethanol, wetting or emulsifying agents, pH buffering substances, or the like. Suitable carriers are typically large, slowly metabolized molecules such as proteins, polysaccharides, polylactic acids, polyglycolic acids, polymeric amino acids, amino acid copolymers, lipid aggregates, or the like.

The term "pharmaceutically acceptable" means a non-toxic material that does not interfere with the effectiveness of the biological activity of the MVA according to the present invention. The characteristics of the carrier will depend on the route of administration. The pharmaceutical composition may further contain other agents which either enhance the activity or use in treatment. Such additional factors and/or agents may be included in the pharmaceutical composition to be applied for the method for immunization according to the present invention to produce a synergistic effect or to minimize side-effects. Techniques for formulation and administration of the MVA according to the invention may be found in "Remington's Pharmaceutical Sciences", (Muck Publishing Gompany, Easton, Pa., latest edition).

For the preparation of vaccines, the recombinant HA-MVA virus according to the invention can be converted into a physiologically acceptable form. This can be done based on the experience in the preparation of poxvirus vaccines used for vaccination against smallpox (as described by Stickl, H. et al. 1974, Dtsch. med. Wschr. 99, 2386-2392).

For example, the purified virus can be stored at −80° C. with a titre of $5 \times 10^8$ $TCID_{50}$/ml formulated in about 10 mM Tris, 140 mM NaCl pH 7.4. For the preparation of vaccine shots, e.g., $10^2$-$10^8$ particles of the virus can be lyophilized in 100 ml of phosphate-buffered saline (PBS) in the presence of 2% peptone and 1% human albumin in an ampoule, preferably a glass ampoule. Alternatively, the vaccine shots can be produced by stepwise freeze-drying of the virus in a formulation. This formulation can contain additional additives such as mannitol, dextran, sugar, glycine, lactose or polyvinylpyrrolidone or other aids such as antioxidants or inert gas, stabilizers or recombinant proteins (e.g. human serum albumin) suitable for in vivo administration. The glass ampoule is then sealed and can be stored between 4° C. and room temperature for several months. However, as long as no need exists, the ampoule is stored preferably at temperatures below −20° C.

For vaccination or therapy, the lyophilisate can be dissolved in an aqueous solution, preferably physiological saline or Tris buffer, and administered either systemically or locally, i.e. parenteral, subcutaneous, intravenous, intramuscular, or any other path of administration known to the skilled practitioner. The mode of administration, the dose and the number of administrations can be optimized by those skilled in the art in a known manner. However, most commonly a patient is vaccinated with a second shot about one month to six weeks after the first vaccination shot.

For a seasonal flu vaccine, a polyvalent HA-MVA comprising HA antigens from multiple influenza viruses is preferred. For example, the MVA can comprise HA antigens from H3N2, H1N1, vH1N1, and from strains of B-Victoria and/or B-Yamagata lineages. Especially preferred are trivalent and quadrivalent vaccines. Preferably, the vaccine is broadly reactive against at least 3 seasonal subtypes of influenza A and B. The seasonal flu vaccine preferably includes internal influenza virus antigens to induce strong CTL responses.

In a most preferred embodiment, the vaccine comprises HA, NA, M2, PB1, NP, and M1 antigens. Preferably, the influenza virus antigens are inserted into 2 or 3 insertion sites in the MVA. Most preferably the type A HA genes and one type B HA gene are inserted into a single site in the recombinant genome to facilitate adaptation of the vaccine to genetic drift of the seasonal influenza virus strains. The seasonal flu vaccine is preferably used for priming in naïve children less than 5, 4, 3, or 2 years of age, and for boosting in non-naïve children and in adults.

For a pandemic flu vaccine, a polyvalent HA-MVA comprising HA antigens from multiple influenza type A viruses is preferred. For example, the MVA can comprise HA antigens from at least 2 of the 4 HA clades according to Russell et al. 2004 (i.e., H9, H1, H3, and H7 clades). For example, the MVA can comprise H9, H5, H2, and H7 HA antigens. A library of vaccines can be constructed that can cover all 16 HA subtypes with 3 or 4 vaccines. Especially preferred are trivalent and quadrivalent vaccines. The pandemic flu vaccine preferably includes internal influenza virus antigens to induce strong CTL responses.

In a most preferred embodiment, the vaccine comprises HA, NA, M2, PB1, NP, and M1 antigens. Preferably, the influenza virus antigens are inserted into 2, 3, 4, or 5 insertion sites in the MVA. The pandemic flu vaccine is preferably administered as a pre-pandemic vaccination, as a targeted vaccination for early responders, or as a post-exposure prophylaxis.

Kits Comprising HA-MVA Viruses

The invention further provides kits comprising an HA-MVA virus. The kit can comprise one or multiple containers or vials of the HA-MVA virus, together with instructions for the administration of the virus to a subject. In a preferred embodiment, the subject is a human. The instructions can indicate that the HA-MVA virus is administered to the subject in a single dosage, or in multiple (i.e., 2, 3, 4, etc.) dosages. The instructions can indicate that the HA-MVA virus is administered in a first (priming) and second (boosting) administration to naïve or non-naïve subjects.

Accordingly or alternatively, the invention provides a kit for prime/boost immunization comprising the recombinant MVA virus and/or the vaccine or pharmaceutical composition including the recombinant MVA virus for a first inoculation ("priming inoculation") in a first vial/container and for a second inoculation ("boosting inoculation") in a second vial/container.

The present invention also relates also to a vaccination kit with the vaccine, pre-filled syringes with the vaccine and other modes of storage and application.

Methods of Immunization with HA-MVA Viruses

The method for immunization according to the present invention will make use of a therapeutically effective amount of the MVA. A therapeutically effective dose further refers to that amount of the compound/ingredient sufficient to result in amelioration of symptoms, e.g. treatment, healing, prevention or amelioration of such conditions. In a preferred embodiment the immunization may be both prophylactic and/or therapeutic.

The invention provides methods for immunizing a subject animal, including birds. Preferably, the animal is a mammal, including rats, rabbits, pigs, mice, and humans comprising administering a dosage of an HA-MVA to a subject.

Most preferably, the subject is a human. In one embodiment, the subject is an adult. In other embodiments, the subject's age can be less than 5 years, less than 3 years, less than 2 years, less than 15 months, less than 12 months, less than 9 months, less than 6, or less than 3 months. In other embodiments, the subject's age can be from 0-3 months, 3-6 months, 6-9 months, 9-12 months, 1-2 years, or more than 2 years, e.g. 2-5 years.

Preferably, a dosage of an HA-MVA of $10^6$ to $10^9$ $TCID_{50}$ is administered to the subject. More preferably, a dosage of $10^6$ to $5\times10^8$ $TCID_{50}$ is administered to the subject. Most preferably, a dosage of $10^7$ to $10^8$ $TCID_{50}$ is administered to the subject. A preferred dosage for humans comprises $10^7$ $TCID_{50}$ or $10^8$ $TCID_{50}$ of an HA-MVA virus.

The HA-MVA virus can be administered to the subject in a single dosage, or in multiple (i.e., 2, 3, 4, etc.) dosages, in particular to a naïve subject. The HA-MVA virus can be administered in a first (priming) and second (boosting) administration. In one embodiment, the first dosage comprises $10^7$ to $10^8$ $TCID_{50}$ of an HA-MVA virus and the second dosage comprises $10^7$ to $10^8$ $TCID_{50}$ of an HA-MVA virus.

The immunization can be administered either systemically or locally, i.e. parenteral, subcutaneous, intravenous, intramuscular, or any other path of administration known to the skilled practitioner.

The vaccine according to the present invention is, in particular, suitable for the immunization of immune-compromised subjects, including a human.

Further encompassed by the present invention are cells comprising the recombinant MVA according to the present invention, either in vitrolex vivo and/or in vivo. In vitro cells may, for example, be the cell line in which the recombinant virus is amplified and produced, respectively, as, for example, in chicken embryo fibroblast (CEF) cells.

EXAMPLES

Example 1

Generation of MVA-PanFlu

The MVA-PanFlu construct is based on MVA-BN and was generated by 4 consecutive insertions of the foreign genes via homologous recombination. The selection genes were removed by additional recombination reactions. The resulting virus stocks (Premaster) have been extensively tested for virus identity, absence of wild-type or precursor virus, absence of selection genes, correct insertion of the inserts, and transcription of the inserts by RT-PCR. The sequences of all inserts and surrounding MVA-sequences have been verified.

Example 2

Generation of MVA-mBN208A

Figure 2:
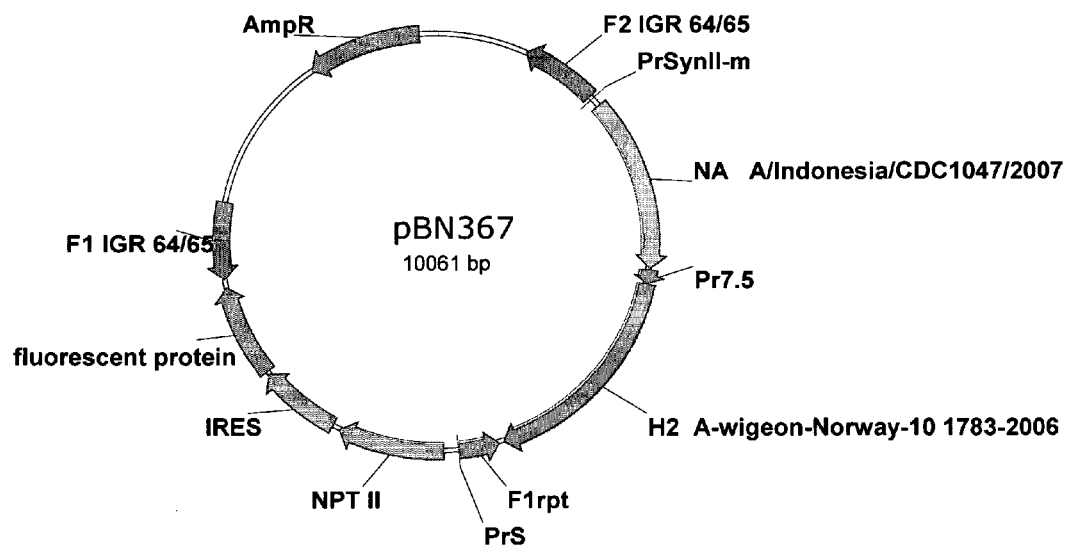
FIG. 2 depicts pBN367.

To generate a recombinant MVA based on the strain MVA-BN, a recombination plasmid for integration of foreign genes into the IGR 64/65 (intergenic region between genes 64 and 65 of MVA-BN, as described in WO 03/097845) was engineered to contain the neuraminidase gene and the H2 gene each under control of a promoter for poxyiral expression. This recombination plasmid pBN367 (FIG. 2.) was used for homologous recombination in CEF cells with MVA-BN. The resulting recombinant virus MVA-mBN208A was plaque purified twice and used as the basis to integrate the next insertion. The selection cassette was deleted during generation of MVA-mBN209B. Generally, "A" as the last letter of a virus name designates a recombinant virus still containing a selection cassette whereas "B" as last letter in a virus name designates viruses where the selection cassette has been deleted.

Example 3

Generation of MVA-mBN209B

Figure 3:
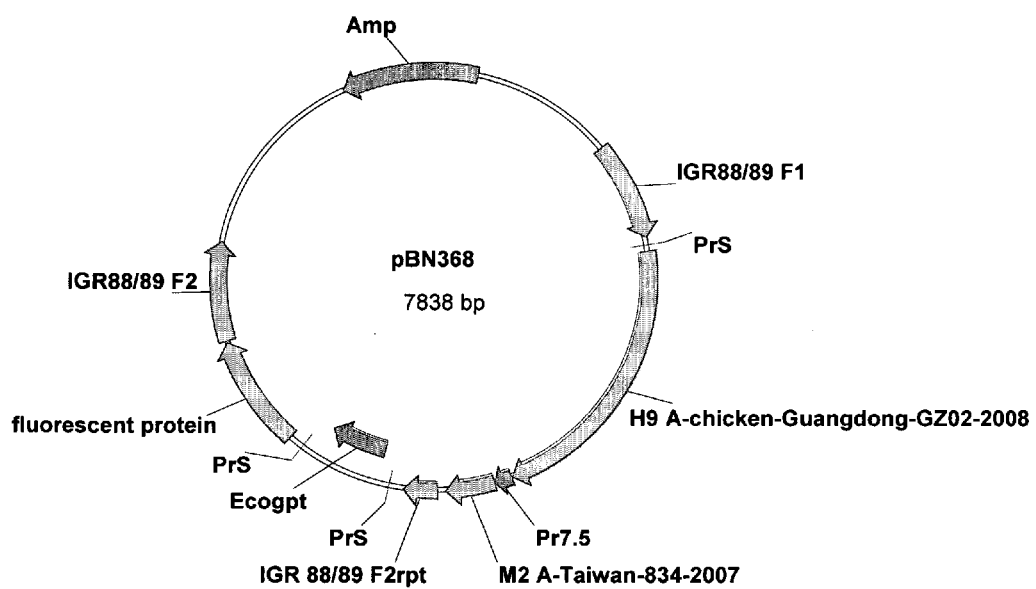
FIG. 3 depicts pBN368.

To generate the recombinant MVA-mBN209B, (based on MVA-mBN208A), a recombination plasmid for integration of foreign genes into the IGR 88/89 (intergenic region between genes 88 and 89 of MVA-BN, as described in WO 03/097845) was engineered to have the H9 gene and the M2 gene each under control of a promoter for poxyiral expression. This recombination plasmid pBN368 (FIG. 3.) was used for homologous recombination in CEF cells with MVA-mBN208A. The resulting recombinant virus MVA-mBN209B was plaque purified five times after the loss of the selection genes and used as the basis to integrate the next insertion. The production of a Premaster of MVA-mBN209 with an adequate viral titer (which means at least $1 \times 10^7$ viral particles/ml) needed several rounds of additional amplification before the final Premaster with a viral titer of $4.6 \times 10^7$/ml could be generated.

Example 4

Generation of MVA-mBN207B

To generate the recombinant MVA-mBN207B, (based on MVA-mBN209B), a recombination plasmid for integration of foreign genes into the IGR 148/149 (intergenic region between genes 148 and 149 of MVA-BN, as described in WO 03/097845) was engineered to have the H5 gene and a fusion gene (consisting of M1, PB1 and NP) each under control of a promoter for poxyiral expression. This recombination plasmid pBN366 (FIG. 1.) was used for homologous recombination in CEF cells with MVA-mBN209B. The resulting recombinant virus MVA-mBN207B was plaque purified 7 times after the loss of the selection genes and used as the basis to integrate the next insertion.

In order to identify optimal production conditions growth studies had to be done. A titer of $2.87 \times 10^7$/ml could be reached after infection with M01=0.1 at 30° C. in VP-SFM medium with pH5.2 for 4 days.

Example 5

Generation of MVA-mBN210B

Figure 4:
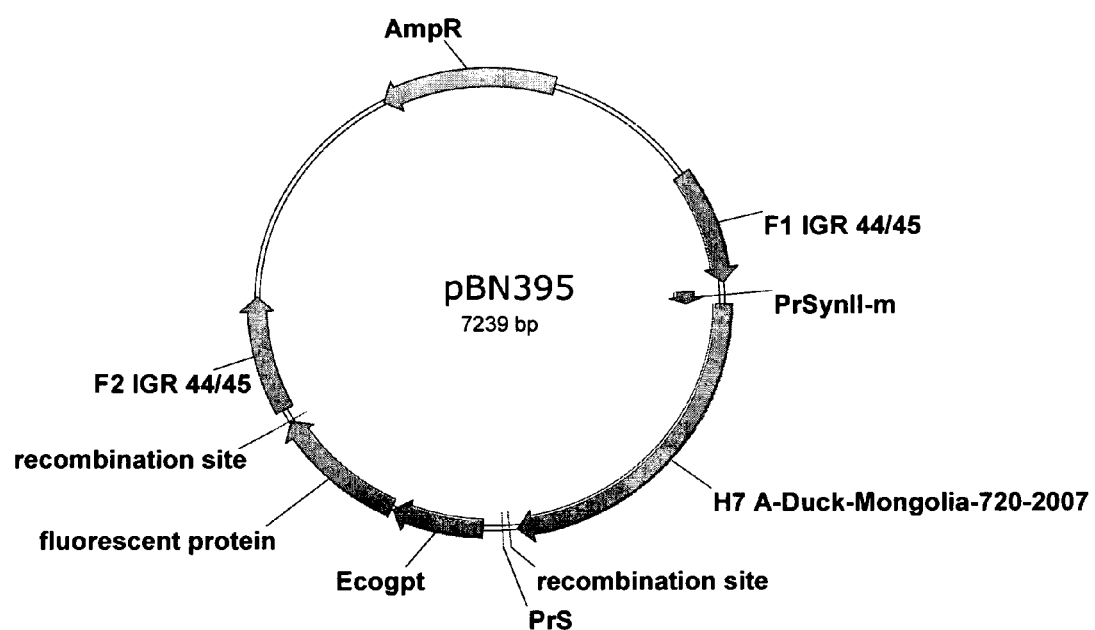
FIG. 4 depicts pBN395.

To generate the recombinant MVA-mBN210B, (based on MVA-mBN207B), a recombination plasmid for integration of foreign genes into the IGR 44/45 (intergenic region between genes 44 and 45 of MVA-BN, as described in WO 03/097845) was engineered to have the H7 gene under control of a promoter for poxyiral expression. This recombination plasmid pBN395 (FIG. 4.) was used for homologous recombination in CEF cells with MVA-mBN207. The resulting recombinant virus MVA-mBN210 (FIG. 5.) was plaque purified five times after loss of the selection genes. A premaster virus stock with adequate viral titer, $4.3 \times 10^7 \text{TCID}_{50}$/ml, could be generated at 30° C.

Example 6

Generation of MVA-FluSeasonal

The MVA-FluSeasonal construct MVA-mBN242 (FIG. 8.) is based on MVA-BN and was generated by 2 consecutive insertions of the foreign genes via homologous recombination. The selection genes will be removed by additional recombination reactions.

Example 7

Generation of MVA-mBN241A

Figure 7:
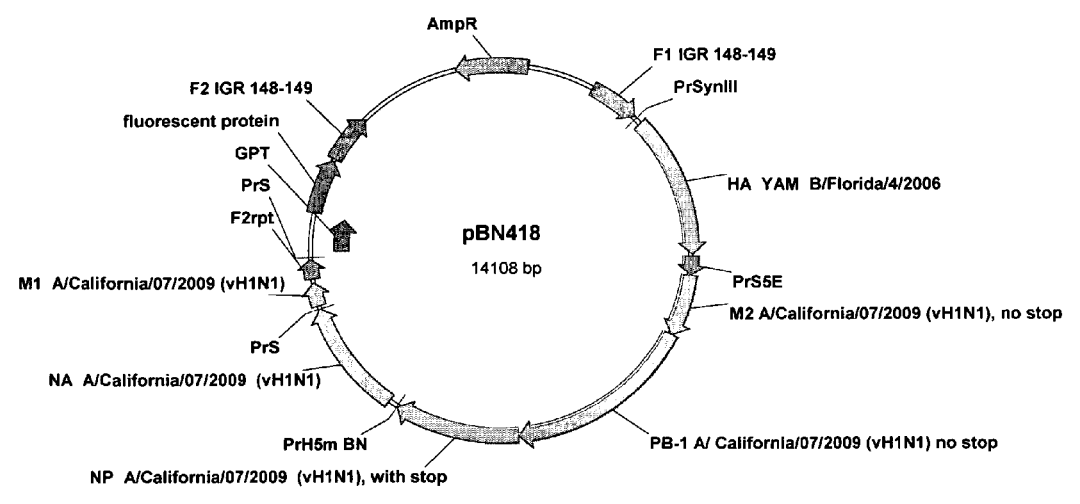

To generate a recombinant MVA based on the strain MVA-BN, a recombination plasmid for integration of foreign genes into the IGR 148/149 (intergenic region between genes 148 and 149 of MVA-BN, as described in WO 03/097845) was engineered to have (1) the HA gene of an influenza virus type B Yamagata lineage (B/Florida/4/2006) and (2) the fusion gene consisting of M1, PB1 and NP and (3) the neuraminidase gene and (4) the M2 gene and each under control of a promoter for poxyiral expression. This recombination plasmid pBN418 (FIG. 7.) was used for homologous recombination in CEF cells with MVA-BN. The resulting recombinant virus MVA-mBN241A was plaque purified twice and used as the basis to integrate the next insertion. For the generation of the MVA-mBN242 with two insertions, the selection cassette will be deleted during generation of MVA-mBN242B. For the generation of MVA-mBN241B, a recombinant virus with one insertion, the selection cassette has been deleted by a second step of homologous recombination.

Example 8

Generation of MVA-mBN242B

Figure 6:
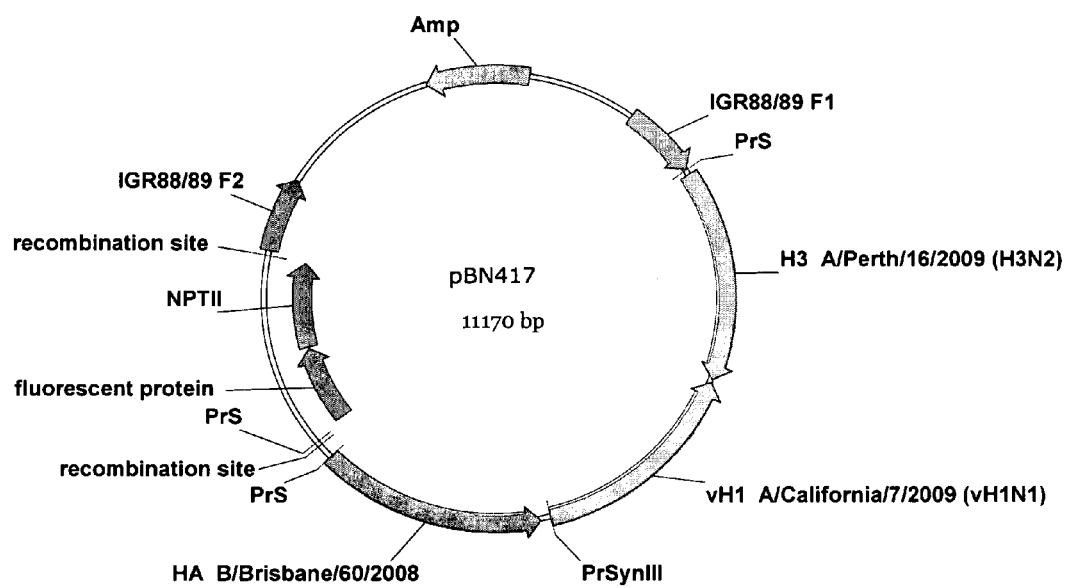
FIG. 6 depicts pBN417.
Figure 8:
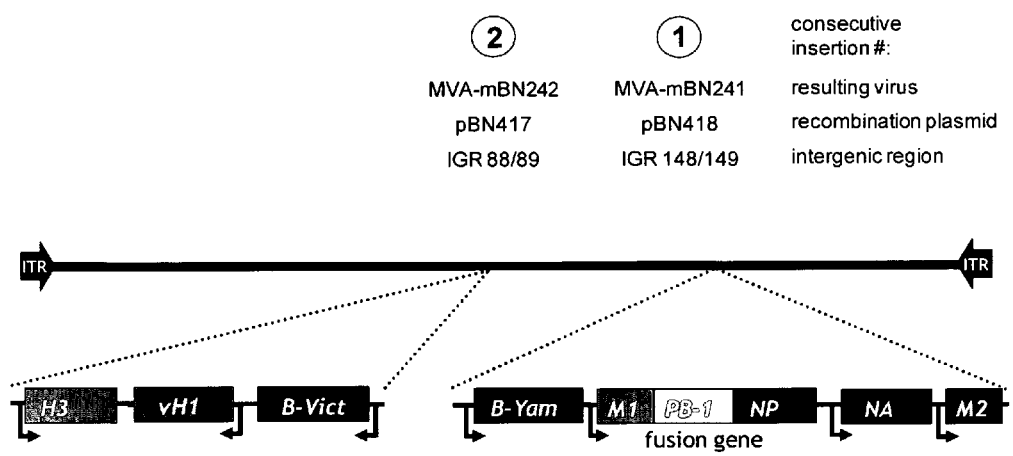
FIG. 8 depicts MVA-FluSeasonal

To generate a recombinant MVA based on the strain MVA-BN, a recombination plasmid for integration of foreign genes into the IGR 88/89 (intergenic region between genes 88 and 89 of MVA-BN, as described in WO 03/097845) was engineered to have (1) the H3 gene and (2) the vH1gene and (3) the HA gene of an influenza virus type B Victoria lineage (B/Brisbane/60/2008) each under control of a promoter for poxyiral expression. This recombination plasmid pBN417 (FIG. 6.) was used for homologous recombination in CEF cells with MVA-mBN241A. The resulting recombinant virus MVA-mBN242A was plaque purified. The selection cassette was deleted via recombination during generation of MVA-mBN242B. The recombinant virus for use as a seasonal flu vaccine is depicted in FIG. 8.

The invention clamied is:

1. A modified vaccinia virus Ankara (MVA) comprising at least 11,000 nucleotides of influenza nucleic acid sequences encoding at least 5 external influenza virus antigens and at least 3 internal influenza virus antigens, wherein the nucleic acid sequences encoding the antigens are inserted into at least two MVA insertion sites,
    wherein the external influenza virus antigens comprise at least 3 different hemagglutinin antigens selected from hemagglutinin 2 (H2), hemagglutinin 9 (H9), hemagglutinin 5 (H5), and hemagglutinin 7 (H7) antigens.

2. The MVA virus of claim 1, wherein the MVA virus comprises nucleic acid sequences encoding at least 6 external influenza virus antigens.

3. The MVA virus of claim 1, wherein the nucleic acid sequences encoding the antigens are inserted into at least 3 MVA insertion sites.

4. MVA virus of claim 2, wherein the nucleic acid sequences encoding the antigens are inserted into at least 3 MVA insertion sites.

5. The MVA virus of claim 1, wherein the nucleic acid sequences encoding the antigens are inserted into at least 4 MVA insertion sites.

6. The MVA virus of claim 2, wherein the nucleic acid sequences encoding the antigens are inserted into at least 4 MVA insertion sites.

7. The MVA virus of claim 1, wherein the external influenza virus antigens are hemagglutinin 2 (H2), hemagglutinin 9 (H9), hemagglutinin 5 (H5), neuraminidase (NA), and matrix protein 2 (M2) antigens.

8. The MVA virus of claim 2, wherein the external influenza virus antigens are H2, H9, H5, H7, NA, and M2 antigens.

9. The MVA virus of claim 1, wherein the internal influenza virus antigens are matrix protein 1 (M1), polymerase basic protein 1 (PB-1), and nucleoprotein (NP) antigens.

10. The MVA virus of claim 2, wherein the internal influenza virus antigens are M1, PB-1, and NP antigens.

11. The MVA virus of claim 7, wherein the internal influenza virus antigens are M1, PB-1, and NP antigens.

12. The MVA virus of claim 8, wherein the internal influenza virus antigens are M1, PB-1, and NP antigens.

13. The MVA virus of claim 1, wherein the MVA virus used for generating the recombinant virus is MVA-BN or a variant of MVA-BN.

14. The MVA virus of claim 1, wherein the insertion sites are selected from IGR 44/45, IGR 64/65, IGR 88/89, and IGR 148/149 of the MVA virus.

15. The MVA virus of claim 11, wherein the insertion sites are IGR 64/65, IGR 88/89, and IGR 148/149 of the MVA virus.

16. The MVA virus of claim 12, wherein the insertion sites are IGR 44/45, IGR 64/65, IGR 88/89, and IGR 148/149 of the MVA virus.

17. A kit for prime/boost immunization comprising the MVA virus of claim 1 for a first inoculation ("priming inoculation") in a first vial or container and for one or more second inoculations ("boosting inoculation") in a second vial or container.

18. An isolated cell comprising the MVA virus of claim 1.

19. A method for generating a modified vaccinia virus Ankara (MVA) expressing at least 5 external influenza virus antigens and at least 3 internal influenza virus antigens comprising inserting at least 11,000 nucleotides of influenza nucleic acid sequences encoding the antigens into at least two MVA insertion sites and isolating the resultant recombinant virus,
    wherein the external influenza virus antigens comprise at least 3 different hemagglutinin antigens selected from hemagglutinin 2 (H2), hemagglutinin 9 (H9), hemagglutinin 5 (H5), and hemagglutinin 7 (H7) antigens.

20. A method for generating an immune response comprising administering to an animal a modified vaccinia virus Ankara (MVA) comprising at least 11,000 nucleotides of influenza nucleic acid sequences expressing at least 5 external influenza virus antigens and at least 3 internal influenza virus antigens, wherein the nucleic acid sequences encoding the antigens are inserted into at least two MVA insertion sites,
    wherein the external influenza virus antigens comprise at least 3 different hemagglutinin antigens selected from hemagglutinin 2 (H2), hemagglutinin 9 (H9), hemagglutinin 5 (H5), and hemagglutinin 7 (H7) antigens.

* * * * *